United States Patent [19]

Maffetone

[11] Patent Number: 5,084,017
[45] Date of Patent: Jan. 28, 1992

[54] SELF DISABLING, SINGLE USE, HYPODERMIC SYRINGE

[76] Inventor: John Maffetone, 22931 Edmonds Way B22, Edmonds, Wash. 98020

[21] Appl. No.: 419,499

[22] Filed: Oct. 10, 1989

[51] Int. Cl.$^5$ .............................................. A61M 5/00
[52] U.S. Cl. ...................... 604/110; 604/228; 604/210
[58] Field of Search ............ 604/110, 207–210, 604/218, 228, 229

[56] References Cited

U.S. PATENT DOCUMENTS

| | | | |
|---|---|---|---|
| 3,951,146 | 4/1976 | Chiquiar-Arias | 128/218 |
| 3,998,224 | 12/1976 | Chiquiar-Arias | 128/218 |
| 4,391,272 | 7/1983 | Staempfli | 604/110 |
| 4,507,117 | 3/1985 | Vining et al. | 604/196 |
| 4,650,468 | 3/1987 | Jennings, Jr. | 604/110 |
| 4,699,614 | 10/1987 | Glazier | 604/110 |
| 4,731,068 | 3/1988 | Hesse | 604/110 |
| 4,775,363 | 10/1988 | Sandsdalen | 604/110 |
| 4,781,684 | 11/1988 | Trenner | 604/110 |
| 4,801,295 | 1/1989 | Spencer | 604/110 |
| 4,820,272 | 4/1989 | Palmer | 604/110 |
| 4,826,483 | 5/1989 | Molnar, IV | 604/110 |
| 4,840,616 | 6/1989 | Banks | 604/218 |
| 4,874,372 | 10/1989 | McArthur | 604/228 |
| 4,906,231 | 3/1990 | Young | 604/110 |
| 4,923,443 | 5/1990 | Greenwood | 604/228 |
| 4,932,941 | 6/1990 | Min | 604/218 |

FOREIGN PATENT DOCUMENTS

| | | | |
|---|---|---|---|
| 8810127 | 12/1988 | World Int. Prop. O. | 604/110 |
| 8900432 | 1/1989 | World Int. Prop. O. | 604/110 |
| 8904185 | 5/1989 | World Int. Prop. O. | 604/110 |

*Primary Examiner*—C. Fred Rosenbaum
*Assistant Examiner*—Sharon Finkel

[57] ABSTRACT

A single-use, hypodermic syringe which disables itself during its initial application thereby preventing any subsequent use of the syringe. The working parts of the invention are designed to separate automatically when the syringe is oriented into the solution dispensing mode. These separated parts prevent subsequent aspiration of solutions into the syringe thereby rendering the syringe inoperable and unuseable after its initial use.

15 Claims, 12 Drawing Sheets

SELF DISABLING, SINGLE USE, HYPODERMIC SYRINGE

BACKGROUND

The growing problem of the transmission of infectious disease via contaminated syringes has established a need for a bonified, single-use, disposable syringe which cannot, under any circumstances, be re-used after its initial application.

In an attempt to address this problem, various so-called "single-use" and "disposable" hypodermic syringes are presently being proposed to the medical products industry. However, these syringes cannot truly be categorized as "single-use" as most share common design characteristics that permit re-use if the syringe is not consciously and discriminately disabled immediately after initial use.

Some of the major shortcomings of these type designs include the fact that these type syringes remain functionally operable after the initial solution has been dispensed so that the medical practitioner must make a concious effort to remember to manually disable the syringe before discarding it. It is obvious, due to the hectic pace of the health professional's day, that there will be many occasions when he will not disable or discard the used syringe and inadvertently place it aside, making it available for re-use and possibly contaminating a subsequent patient. Also, once used and discarded, syringes can be recovered from waste receptacles located outside the health facility by individuals intending to modify these syringes for repeated use, as in needle sharing and illicit drug use.

An analysis of the problems and shortcomings inherent in the above mentioned syringes has led to the development of the present invention: a bonified, single-use, disposable, hypodermic syringe which is designed to self-disable during its initial and only application. This unique design feature, together with its tamper-proof encasement, automatically renders the aspirating function of the syringe permanently inoperable once the actuating rod is orientated into the solution dispensing mode. These design features completely eliminate the need for the health professional's concern in handling or misplacing, a used, possibly contaminated syringe.

Thus, the present invention can be used to aspirate and dispense a solution only once and any further use is absolutely precluded under any circumstances.

The present invention is a dramatic improvement over the prior art as it guarantees a new, previously unused, antiseptic syringe with a burr-free needle-point for each new, individual patient. The possibility of contamination of this invention by inadvertent repeated use is eliminated as the entire syringe assembly is simply not re-usable nor can it be modified before or after its initial use. The present invention would therefore also help greatly in the flight against Aids by eliminating the dangerous practice of needle sharing among illicit drug users.

Those in the medical and health professions familiar with the present state of the art would find it cost effective and prophylactically expedient to have and use an antiseptically assured, self disabling, non-reusable, disposable hypodermic syringe.

PRIOR ART

Several types of so-called non-reusable disposable syringes have been proposed to the medical products industry. Upon close examination of these syringes it appears that each have common design characteristics which allow the user to bypass the disabling function of the syringe or permit its modification thereby facilitating repeated use. Also, because of inherent design factors, most of these syringes are susceptible to being inadvertently or prematurely disabled prior to their intended use if the user is not aware of or is not properly trained in their specific use.

Typical examples of syringes which contain these alterable characteristics are described in Jennings, U.S. Pat. No. 4,650,468 and in Palmer, U.S. Pat. No. 4,820,272. The Jennings syringe illustrates a safety syringe which may or may not, depending upon the user's discretion, be manually disabled after its initial use. Thus, the syringe can be repeatedly used if the user so desires.

In Palmer, the syringe requires assembly by the user prior to its use. This may not be a problem in a professional clinical setting, but in the wrong hands, the syringe's exposed working parts could be easily modified, thereby allowing repeated use and abuse.

Also, the disabling mechanisms on both of these type syringes can be prematurely engaged prior to their intended use. An inadvertent movement of the actuating rod during preparation or handling of the syringe, can place the locking member of the rod into the locking recess of the barrel tube thereby rendering the syringe ineffective.

This can easily occur with the Palmer type syringe as its locking mechanism is located in the forward portion of the syringe and designed to engage when the actuating rod is pushed all the way forward into the syringe barrel tube. This feature also creates a conflicting situation, as most, if not all, health professionals, push the actuating rod all the way to the front of the barrel tube in an attempt to expel the air from the solution chamber prior to aspirating a solution into the syringe. Thus, before aspiration, when attempting to clear the Palmer syringe of unwanted air by pushing the actuating rod forward, the user may accidently engage the locking mechanism of the syringe.

In the Jennings syringe, the disabling mechanism is located in the rearward portion of the syringe's barrel tube and is designed to activate when the user intentionally pulls the actuating rod to the rear of the syringe, after the solution has been dispensed to a patient. However, this locking mechanism can also be accidently activated while the user is pulling the actuating rod to the rear while attempting to initially aspirate a solution into the syringe.

Thus, the effectiveness and integrity of both these type syringes can easily be compromised by intentional modification, alteration, or by inadvertent, premature engagement of the locking or disabling device of the syringe.

BRIEF SUMMARY OF THE PRESENT INVENTION

The disposable syringe illustrated by the present invention provides a convenient, inexpensive, time saving, prophylactic means of administering drugs and solutions hypodermically. Its unique design and self-disabling feature, necessarily dictates that the entire syringe assembly be used only once and then be discarded. The sterility of each new syringe and the effective sharpness of each new needle point are thereby assured. Taken from its sterile container and used for only one application, the entire syringe must then be disposed of as the syringe's piston is designed to separate automatically from the actuating rod when the syringe is manually orientated into the solution dispensing mode. As a result of this separation, the detached piston can only be pushed forward by the actuating rod in dispensing the initially aspirated solution, but cannot be subsequently pulled to the rear if a second aspiration is attempted.

Also, the tamper-proof design of the present invention prevents the unit from being taken apart or modified for illicit use. The only way into the working parts of the present invention is to break apart or destroy the components of the syringe and render the entire syringe useless. The present invention also incorporates a safety shoulder which prevents inadvertent disabling of the syringe prior to its intended use.

Briefly, the sequence of operations of the present invention is as follows: When ready for use, a new, factory assembled, sterile syringe is removed from its container. The actuating rod with connected piston is disposed in the forward portion of the barrel tube (FIG. 2). The integral teeth of the movable, actuating rod are engaged with the tooth stops of the fixed rod housing and the guide pin is in contact with the safety shoulder, preventing premature disablement of the syringe by inadvertent rotative movement of the rod.

With the rod teeth engaged with the housing's tooth stops as in a ratchet and pawl configuration, the actuating rod can now only move in the rearward direction for the initial solution aspiration. (Drawing FIGS. 2, 3, 7, 10 and 18).

The needle portion of the syringe is then inserted into a solution bottle and the plunger assembly, (actuating rod with connected piston) is drawn to the rear to aspirate solution into the syringe. The actuating rod teeth engage in the rod housing's tooth stops with a snug, force fit and the teeth pass through the stops with a ratchet and pawl type clicking effect as the plunger assembly is pulled to the rear. Rearward travel of the actuating rod is guided by the stationary guide pin which is seated in guide track "A". At factory assembly, the guide pin is initially set into the actuating rod's guide track "A" (solution aspiration track) and the guide pin abuts the safety shoulder, thereby preventing premature or inadvertent disablement of the syringe by premature rotation of the actuating rod.

The safety shoulder becomes clear of the obstructing pin when the actuating rod is pulled slightly to the rear during initial aspiration. Then, as with any conventional syringe, a solution is aspirated until the desired quantity is contained within the barrel tube. At this point, the actuating rod's rearward travel is manually stopped (FIG. 3).

The next step is to dispense the solution from the present invention into the patient. This requires a forward pushing force applied to the actuating rod. However, forward travel of the actuating rod and piston is blocked by the engagement of the actuating rod teeth in the rod housing as previously noted.

Therefore, to dispense the solution, the actuating rod must be manually rotated 90 degrees clockwise, axially within the inside diameter surface of the barrel tube (FIG. 4).

This rotation of the actuating rod simultaneously accomplishes three major functions:

1. It disengages the actuating rod's teeth from the rod housing thereby rotatively aligning the actuating rod's teeth within the unobstructed sleeve area of the rod housing. This will now allow the rod to travel forward freely when the solution is ready to be dispensed into the patient (FIGS. 4 and 11).

2. Guide track "A" (solution aspiration mode track) is rotated out of engagement with the guide pin while guide track "B" (solution dispensing mode track) is rotated into engagement with the guide pin (Drawing FIGS. 4, 5 and 11).

3. The rotation of the actuating rod simultaneously unseats the rod's locking lug from the piston's lug engagement seat. The locking lug now comes to rest in the disengagement slot and reconnection of the piston to the actuating rod is permanently blocked by the lug return stop 115 of the disengagement slot (FIG. 4 and 17).

The disconnected piston can now only be pushed forward by the actuating rod in dispensing the solution, but cannot be pulled to the rear by the unconnected rod in an attempt to re-fill the syringe (Drawing FIG. 6).

Thus, further use of the syringe is precluded. Any attempt to dismantle the present invention for re-use or re-aspiration will prove fruitless, as the only way into the working parts of the syringe is to destroy the rod housing and barrel tube, rendering the entire syringe assembly useless.

Therefore, after the initial aspiration and dispensing of a solution, the present invention cannot be used a second time and must be discarded.

OBJECTS OF THE PRESENT INVENTION

It is an object of the present invention to provide a single-use, self-disabling, disposable hypodermic syringe which is designed to be used only once and then must be discarded.

It is another object of the present invention to provide each separate patient with a new, previously unused, burr-free, antiseptically assured hypodermic syringe.

It is yet another object of the present invention to provide an easy to use, time saving and labor efficient, disposable hypodermic syringe.

It is another object of the present invention to provide a self-disabling, single-use, disposable hypodermic syringe which is cost effective, both in its use and in its manufacture.

It is another object of the present invention to provide a self-disabling, single-use, disposable hypodermic syringe which is superior to any existing prior art in helping to eliminate the transmission of infection via contaminated syringes.

It is yet another object of the present invention to provide a tamper-proof, single-use, self-disabling, disposable hypodermic syringe which by its inherent design, prevents disassembly, modification or re-use of any of its parts It is another object of the present invention to provide a single-use, self-disabling, disposable hypodermic syringe that is prophylactically superior to any prior art hypodermic syringe available today.

It is another object of the present invention to provide a single-use, self-disabling, disposable hypodermic syringe that cannot inadvertently or prematurely be disabled prior to being used for its intended purpose.

These and other advantages of the present invention will become apparent from the enclosed specifications and accompanying drawings.

BRIEF DESCRIPTION OF THE DRAWINGS

FIGS. 12 and 13 show the spring arm being manually depressed so that the actuating rod sleeve can be slip fitted into the inside diameter surface of the piston. FIG. 14 shows the locking lug detent springing up and locking into place in the piston's lug engagement seat.

DETAILED DESCRIPTION OF THE PRESENT INVENTION

Figure 1:
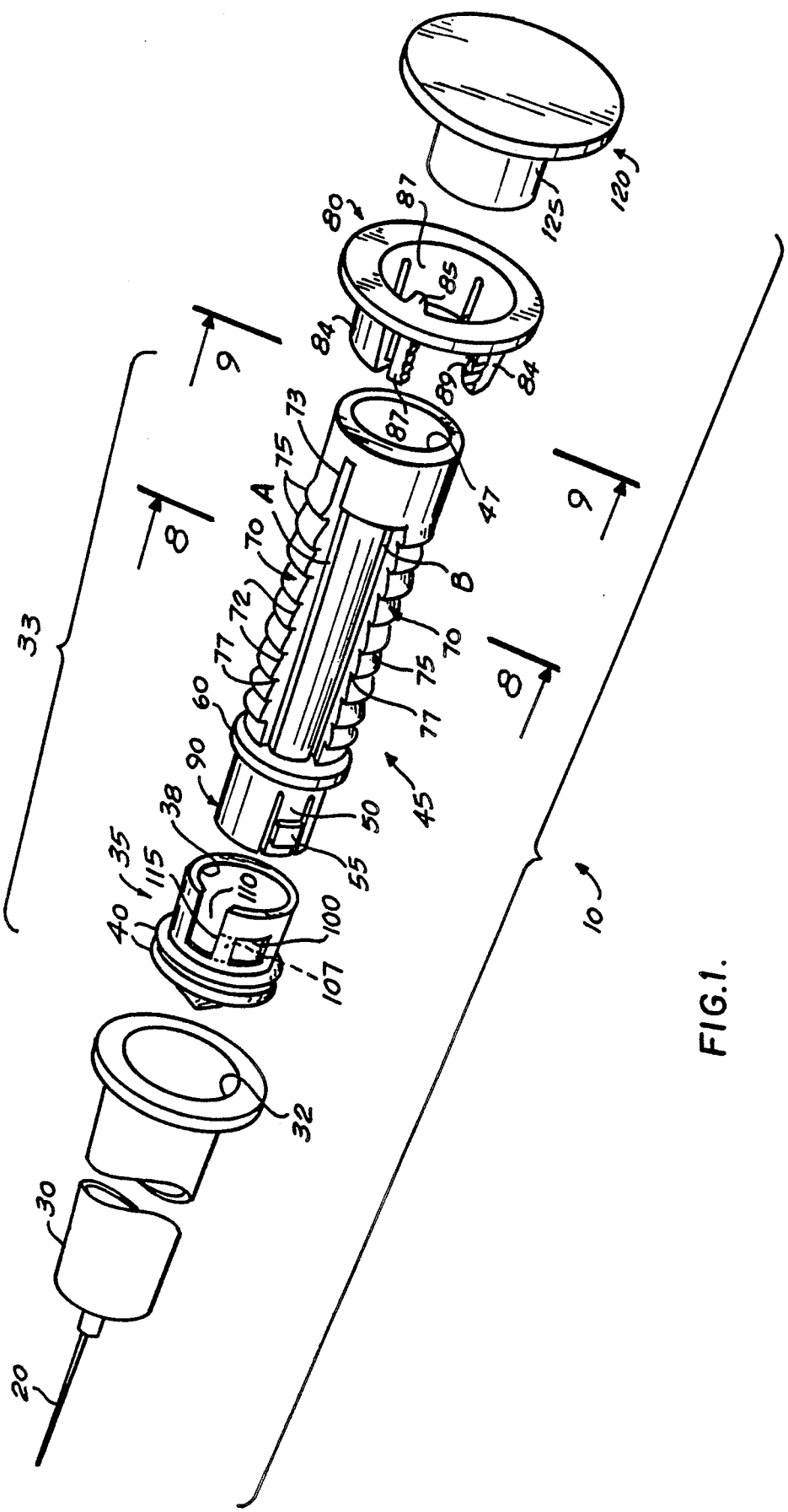
FIG. 1 is an exploded, perspective view of the present invention showing its individual parts.

Referring to Drawing FIG. 1, the self-disabling syringe 10 comprises a hollow barrel tube 30 with permanently affixed hollow hypodermic needle 20.

Plunger assembly 33 incorporates actuating rod 45 and piston 35. Actuating rod 45 incorporates sleeve 90 at its distal end which includes spring arm detent 50 with integral locking lug 55. Travel stop 60 is formed integrally with rod 45 as are actuating rod teeth 70 and guide pin tracks "A" and "B" (tracks "A" and "B" are engaged with guide pin 85 during aspiration and dispensing modes respectively). Safety shoulder 73, is formed as an integral side wall of guide pin track "A".

Piston 35 comprises seals 40, lug engagement seat 100, eccentric underside surface 107 and lug disengagement slot 110, which incorporates, as one of its side walls, lug stop 115.

Rod housing 80 comprises flexure arms 84 and housing sleeves 87. Tooth stops 89 are formed integrally with flexure arms 84 and guide pin 85 is integral with housing sleeve 87.

Shaft 125 of end cap 120 becomes permanently affixed to inside diameter 47 at the proximal end of actuating rod 45.

Figure 12:
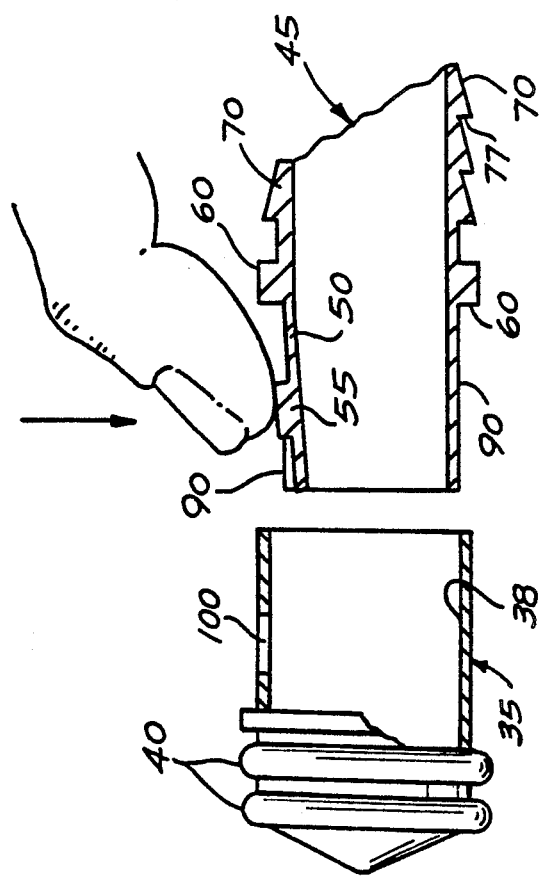

During initial assembly by the manufacturer, as shown in FIG. 12, sleeve 90 with incorporated spring arm 50 and locking lug 55, is slip fit into inner diameter surface 38 of piston 35 by slightly depressing spring arm detent 50 with incorporated lug 55.

Figure 13:
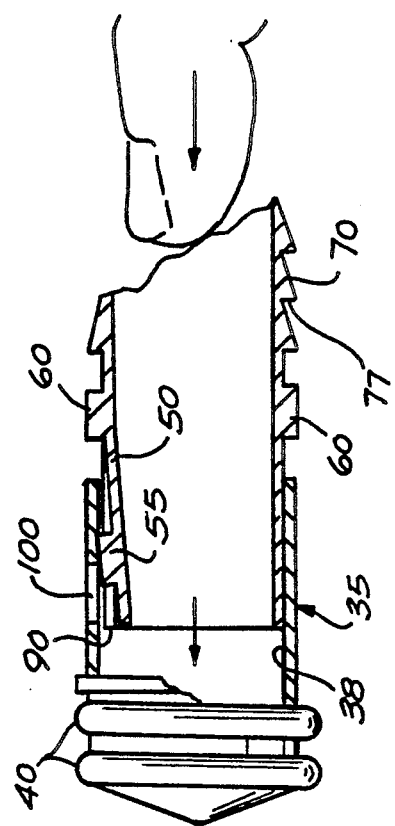
FIGS. 12, 13 and 14 are longitudinal sectional views showing the actuating rod being connected to the piston during initial assembly by the manufacturer.
Figure 14:
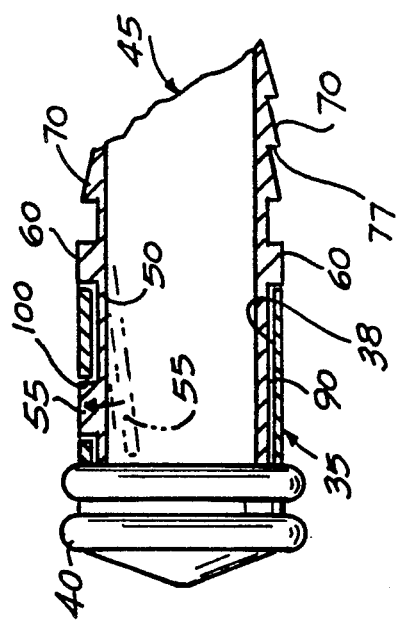

With spring arm detent 50 in the depressed position, sleeve 90 is then pushed forward into inner diameter surface 38 of piston 35 (FIG. 13). As locking lug 55 approaches engagement seat 100, the recoiling action of spring arm 50 forces integral lug 55 up into seat 100, thereby mechanically connecting actuating rod 45 with piston 35 (FIG. 14).

Figure 2:
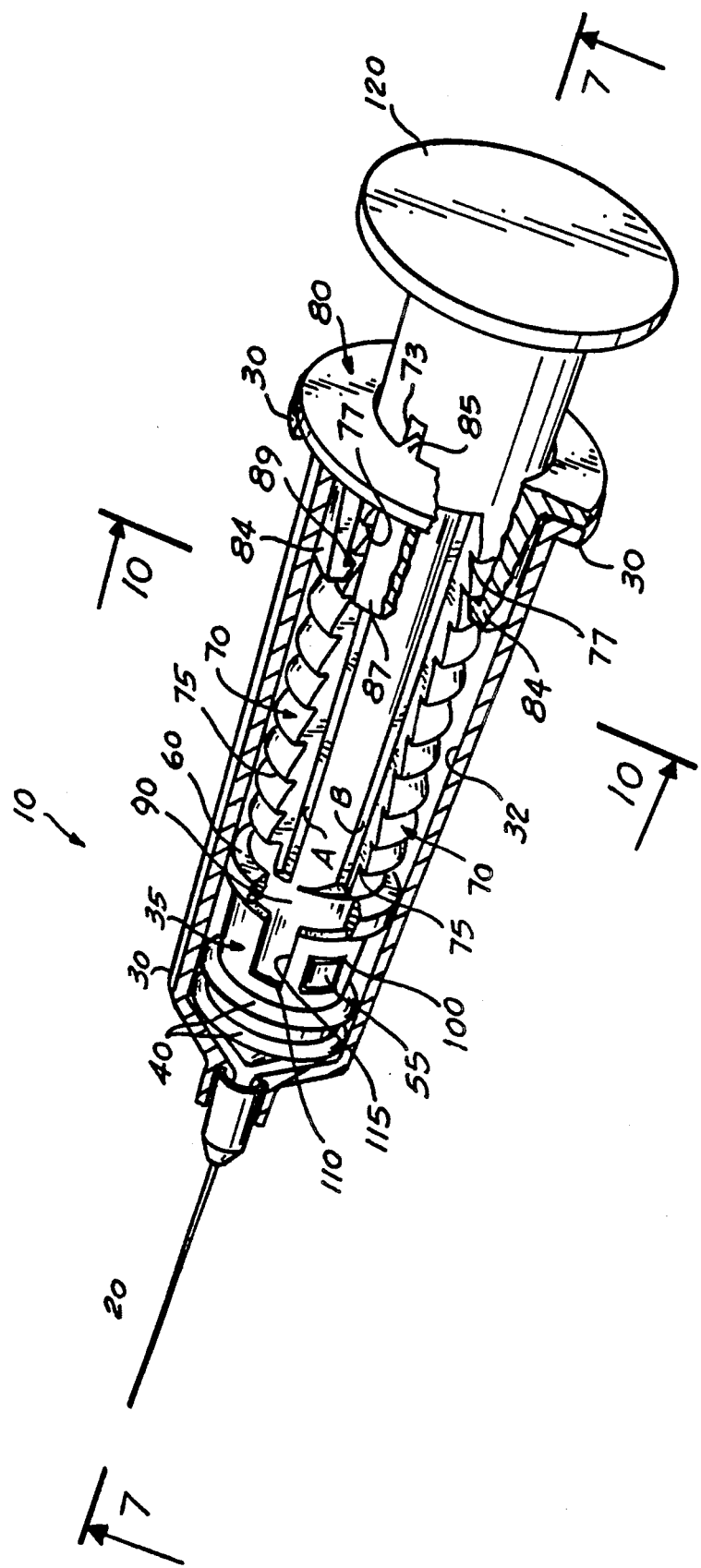
FIG. 2 is a sectional perspective view of the present invention showing the hollow needle attached to the barrel tube. The internal parts are shown assembled within the encasing barrel tube as the syringe is received, ready for use, from the manufacturer. The guide pin is engaged with the safety shoulder thereby preventing inadvertent disablement of the syringe by premature axial rotation of the actuating rod.

Actuating rod 45 and connected piston 35 make up plunger assembly 33 which can now be drawn to the rear as a unit during the aspiration mode. Referring now to FIG. 2, plunger assembly 33 is inserted into rod housing 80. The proximal end of actuating rod teeth 70 are placed into engagement with tooth stops 89 of rod housing 80.

The assembled unit of plunger assembly 33 and rod housing 80, is then inserted into the inside diameter 32 of barrel tube 30. Rod housing 80 is then permanently affixed, by acceptable industry fastening methods, within the proximal end of barrel tube 30 while hollow needle 20 is attached to the distal end of barrel tube 30. End cap shaft 125 of end cap 120 is then permanently affixed to inner diameter surface 47 of actuating rod 45.

Plunger assembly 33 and rod housing 80 are now permanently encapsulated within barrel tube 30 (FIG. 2).

It should be noted that some applications of the present invention may require permanent fixation of hollow needle 20 to barrel tube 30, whereas other applications of the invention may not.

FIG. 2 shows syringe 10, as received from the manufacturer, assembled and ready for use. Piston 35 and actuating rod 45 are connected by locking lug 55 which rests in engagement seat 100. Thus, rod 45 and piston 35, now assembled as plunger assembly 33, can move as a connected unit in the rearward direction during the initial aspiration of a solution.

Guide pin 85 is shown in abutting contact with safety shoulder 73 thus preventing premature axial rotation of actuating rod 45. Rod 45 cannot be rotated into the solution dispensing mode until the safety shoulder 73 is dislodged from the blocking action of the stationary guide pin 85. This dislodging takes place when the plunger assembly 33 is pulled to the rear during initial aspiration of a solution.

Figure 19:
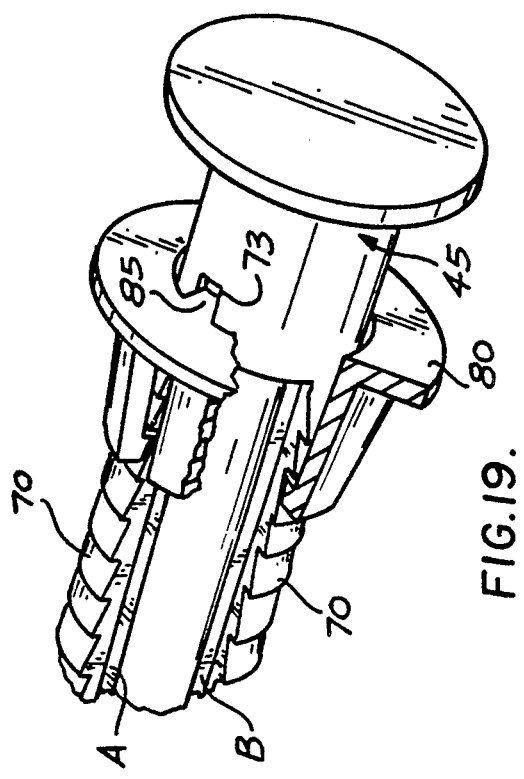
FIGS. 19, 20 and 21 are partial sectional perspective views showing the engagement and disengagement of the safety shoulder with the guide pin. Rotation of the actuating rod is shown in FIG. 21 after the actuating rod has been pulled to the rear as shown in FIG. 20, thereby freeing the safety shoulder from the guide pin during initial aspiration of a solution.
Figure 20:
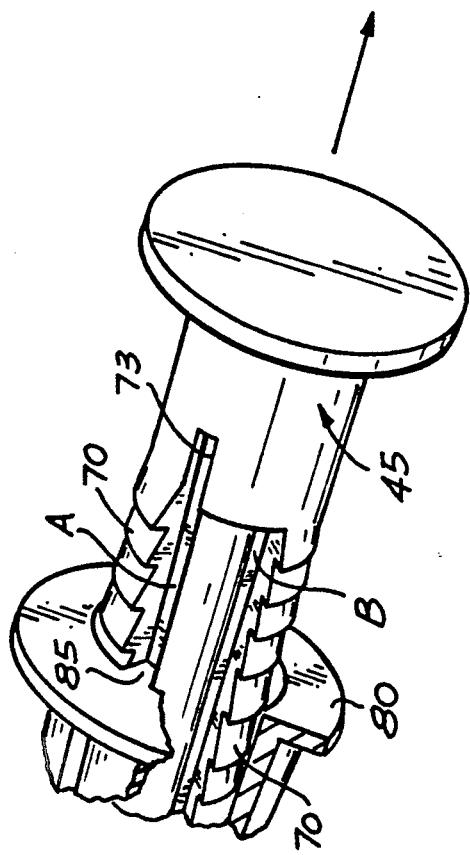
Figure 21:
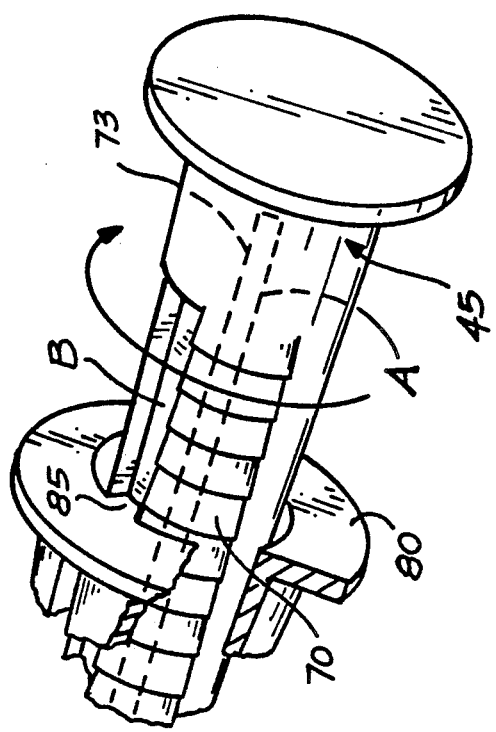

As the safety shoulder 73 clears the guide pin 85, the actuating rod 45 can then be rotated axially, within barrel tube 30, thereby positioning the plunger assembly 33 into the initial solution dispensing mode. (FIGS. 19, 20 and 21).

Figure 3:
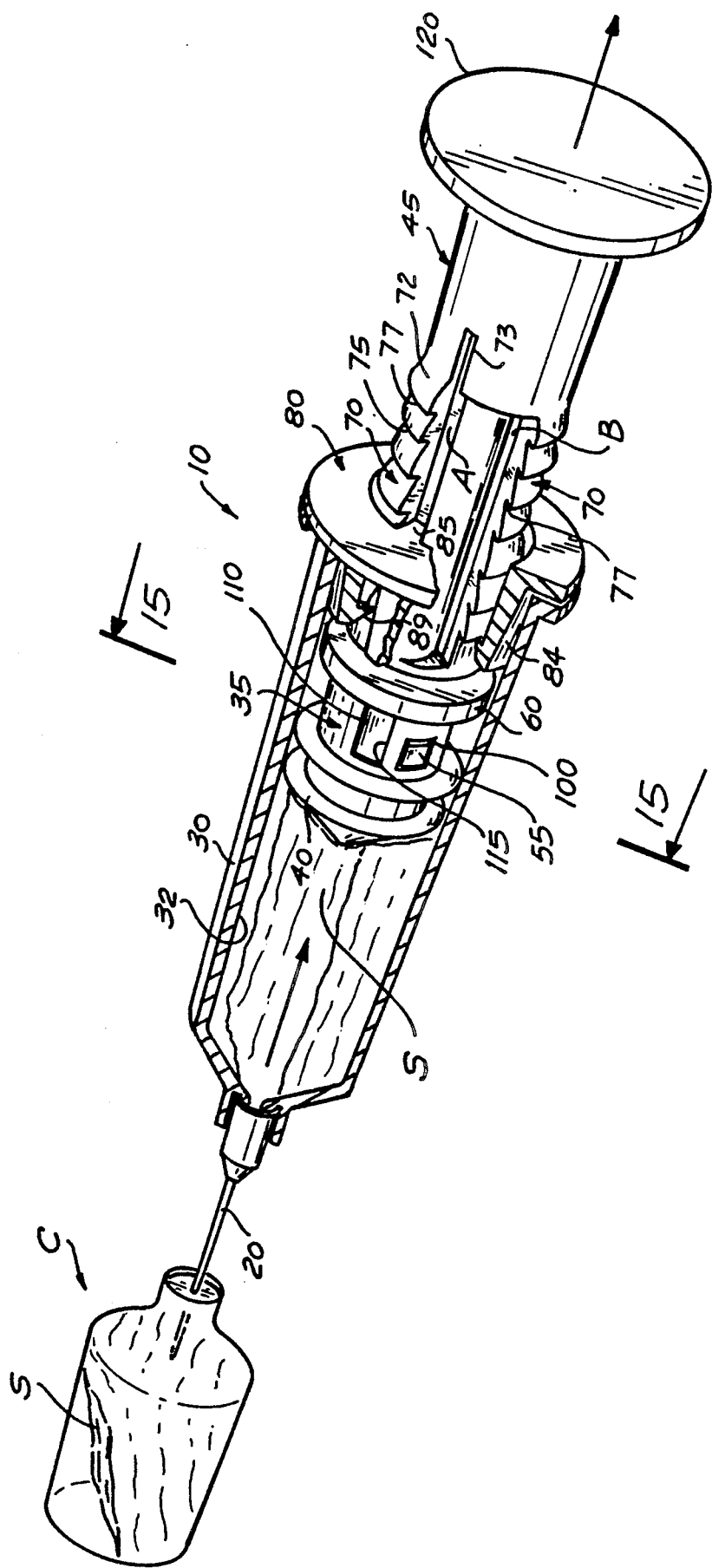
FIG. 3 is a sectional, perspective view of the present invention, showing the needle inserted into a solution bottle. The actuating rod and connected piston are shown being drawn back, aspirating solution into the barrel tube. The actuating rod teeth are shown, being pulled through the rod housing's tooth stops. The safety shoulder is out of engagement with the stationary guide pin and the pin seats in guide track "A" during aspiration of the solution. The actuating rod is now in position to be rotated axially, thereby orientating the rod into the solution dispensing mode.
Figure 18:
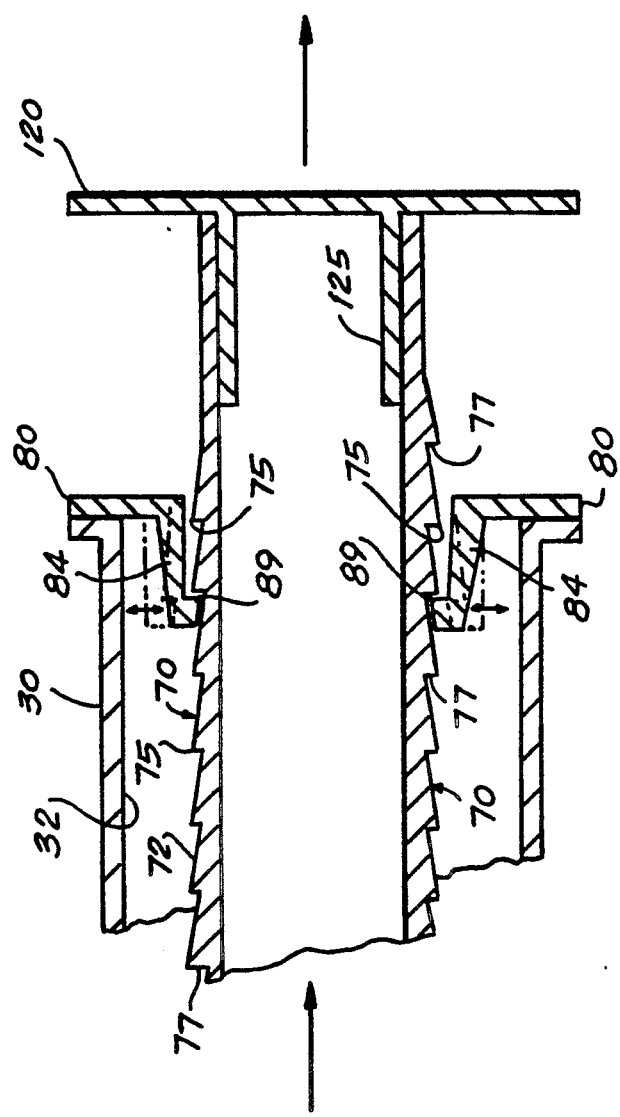
FIG. 18 is a partial longitudinal sectional view of the actuating rod's rearward travel through the rod housing during aspiration of a solution. Expansion and contraction of the flexure arms with incorporated tooth stops are shown as in a ratchet and pawl configuration, as the actuating rod's teeth frictionally slide through the rod housing's tooth stops.

Referring to FIG. 3, solution "S" is being aspirated from solution bottle "C" into barrel tube 30 of syringe 10. During aspiration, as plunger assembly 33 is pulled to the rear, teeth 70 frictionally slide over tooth stops 89. As shown in FIG. 18, flexure arms 84, with integral tooth stops 89, expand centrifugally outward as tooth shoulders 75 of teeth 70 are pulled past tooth stops 89. As dictated by the profile shape of teeth 70, as each tooth shoulder 75 is frictionally forced past tooth stops 89, the recoiling action of flexure arm 84 forces integral tooth stop 89 downward into the tooth waist area 72 of the next approaching actuating rod tooth 70.

Figure 7:
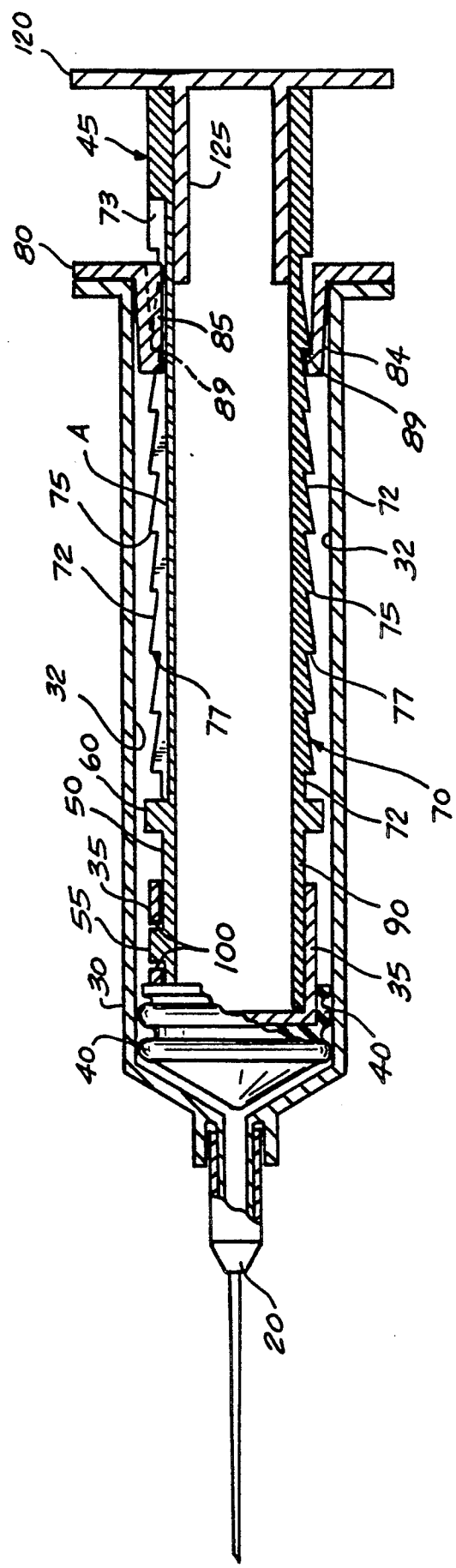
FIG. 7 is a longitudinal sectional view taken along lines 7—7 of FIG. 2.
Figure 10:
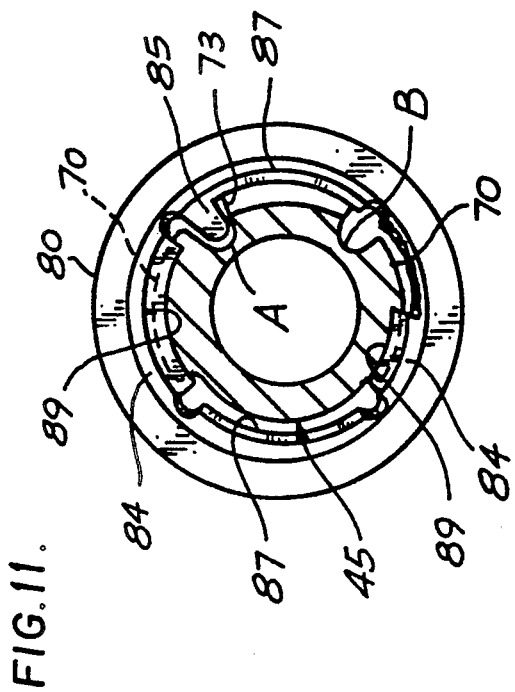
FIG. 10 is a cross-sectional view showing the actuating rod's teeth engaged with the rod housing's tooth stops. The guide pin is shown seated in guide track "A" (solution aspiration track), taken along lines 10—10 of FIG. 2.

A ratchet and pawl effect is thereby created by the tooth stops 89 expanding and contracting with subtle "clicks" as actuating rod teeth 70 are "forced" past tooth stops 89. As each tooth 70 passes through tooth stops 89 during the aspiration mode, bearing surfaces 77 of teeth 70 seat firmly against tooth stops 89, thereby preventing forward travel of plunger assembly 33 (FIGS. 3, 7 and 18).

Therefore, when engaged with tooth stops 89 of housing 80, actuating rod teeth 70 can be pulled rearward past the tooth stops 89 while aspirating a solution, but cannot be pushed forward because of the blocking action of tooth stops 89 against bearing surfaces 77 of teeth 70 (FIGS. 2, 3, 7, 10 and 18). When the desired quantity of solution is aspirated into syringe 10, rearward pulling of plunger assembly 33 is then manually stopped in preparation to dispense solution "S".

Figure 4:
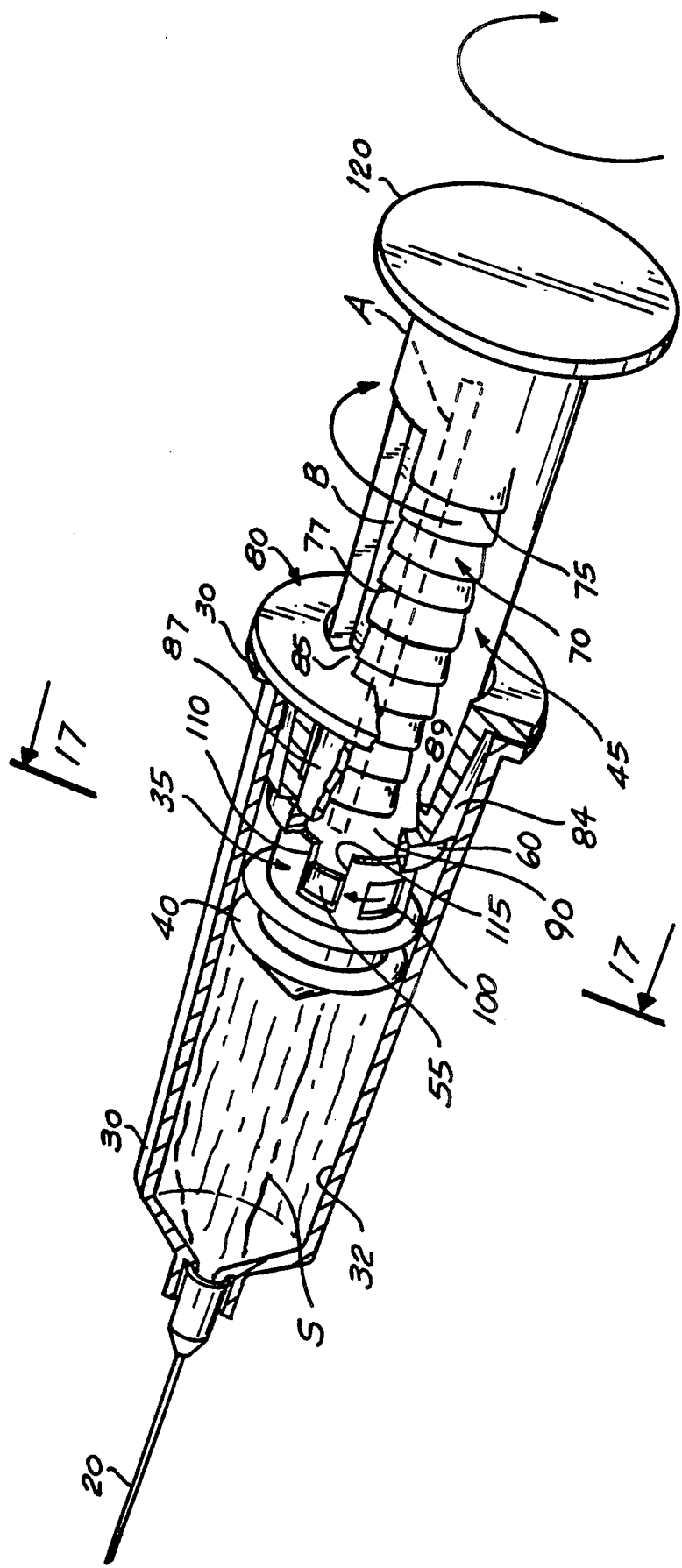
FIG. 4 is a sectional perspective view of the present invention showing the actuating rod, now in the solution dispensing mode, having been manually rotated 90 degrees clockwise, axially, within the inside diameter surface of the piston. The actuating rod teeth are shown disengaged from the rod housing's tooth stops and the actuating rod's locking lug is shown simultaneously disconnected from the piston's locking lug seat. As a result of the rotation of the rod, guide track "B" (solution dispensing track) has been rotated into position with the stationary guide pin. The travel stop abuts the rod housing thereby preventing further rearward travel of the actuating rod.
Figure 5:
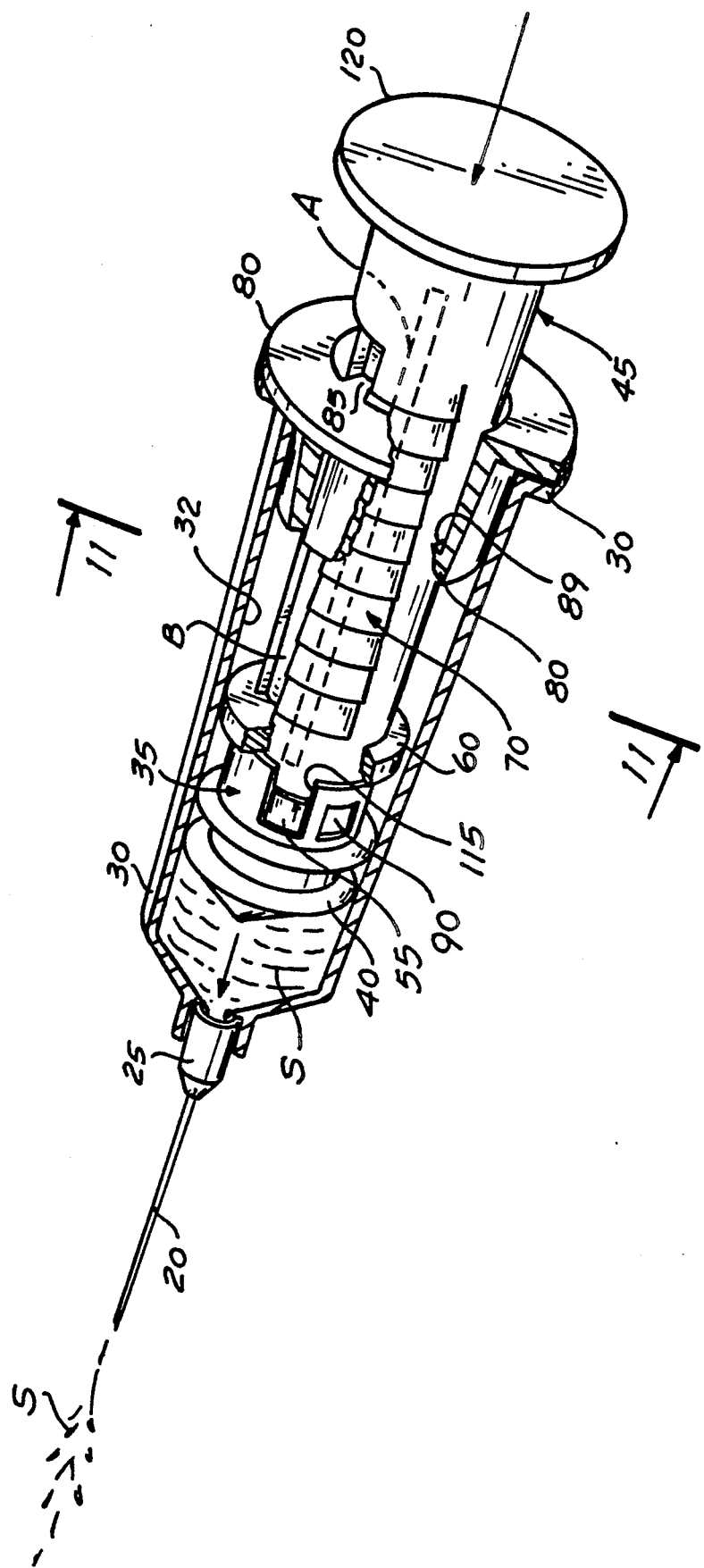
FIG. 5 is a sectional, perspective view, showing both the actuating rod teeth and locking lug disengaged. The rod's teeth have been rotated into the unobstructed sleeve portion of the rod housing. The guide pin is seated in guide track "B" (solution dispensing track) as actuating rod and piston, are pushed forward, dispensing the solution.
Figure 11:
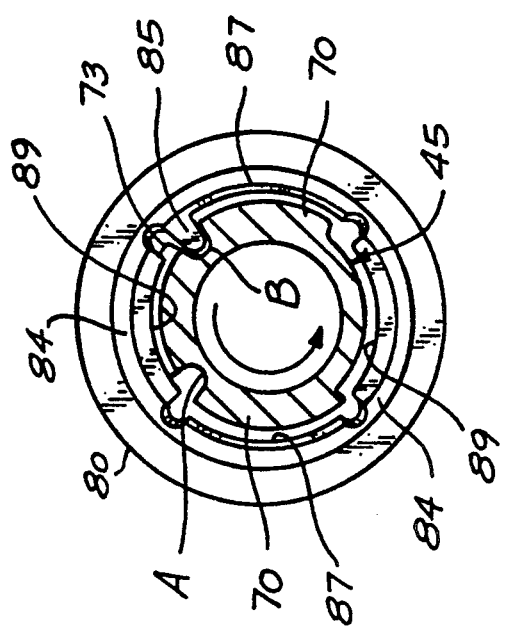
FIG. 11 is a cross-sectional view of the actuating rod's teeth having been rotatively disengaged from the rod housing. The guide pin is now shown seated in guide track "B" (solution dispensing track), taken along lines 11—11 of FIG. 5.
Figure 9:
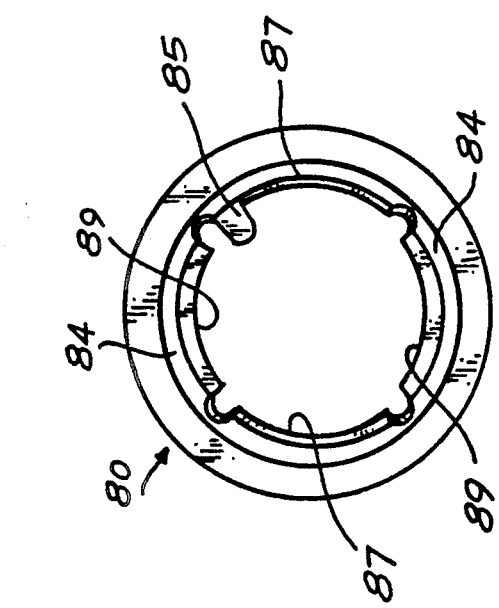
FIG. 9 is a front elevational view of the rod housing showing the housing sleeves with integral guide pin and flexure arms with integral tooth stops, taken along lines 9—9 of FIG. 1.
Figure 8:
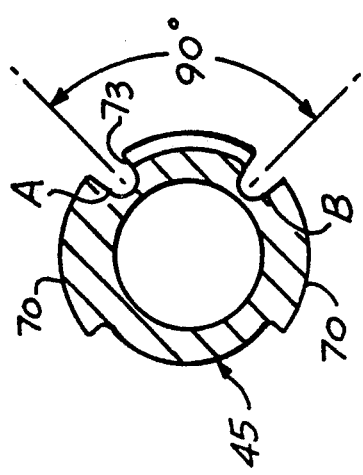
FIG. 8 is a cross-sectional view of the actuating rod showing the rod's teeth and guide track "A" with integral safety shoulder and guide track "B", taken along lines 8—8 of FIG. 1.

To dispense solution "S", bearing surfaces 77 of rod teeth 70, must be rotatively disengaged from tooth stops 89, thereby allowing actuating rod teeth 70 to pass unblocked through rod housing 80. This is accomplished by manually rotating actuating rod 45, ninety degrees clockwise axially within rod housing 80 (FIG. 4). Teeth 70 are thereby rotated out of engagement from tooth stops 89 and become aligned in the smooth, unobstructed areas of housing sleeves 87 (FIGS. 4, 5 and 11). Actuating rod 45 can now travel forward, unobstructed through rod housing 80.

Figure 16:
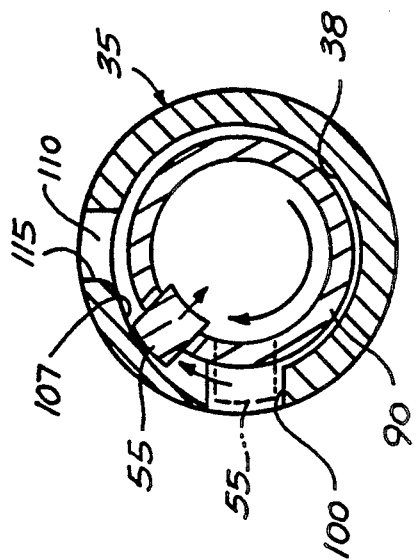
FIG. 16 is a similar cross-sectional view as FIG. 15 but now showing the locking lug moving in a clockwise direction along the eccentric surface of the inside diameter of the piston.
Figure 17:
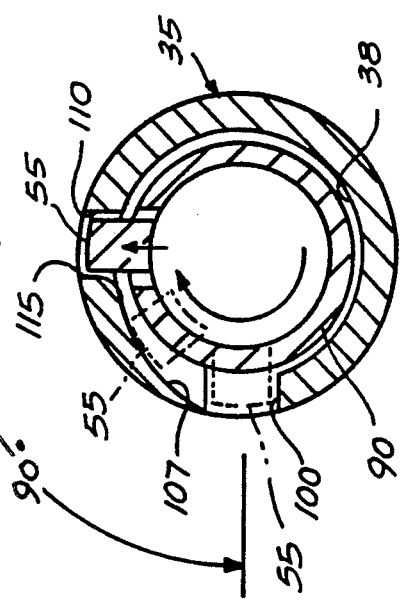
FIG. 17 is a similar cross sectional view as FIG. 16 showing the actuating rod's locking lug coming to rest in the piston's disengagement slot, taken along lines 17—17 of FIG. 4.
Figure 15:
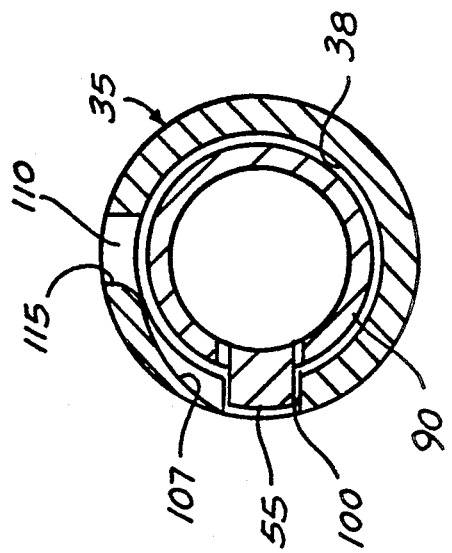
FIG. 15 is a cross-sectional view of the actuating rod sleeve with connected piston, showing the locking lug seated and locked in the engagement seat of the piston, taken along lines 15—15 of FIG. 4.

Referring to FIG. 16, as teeth 70 are being rotatively disengaged from rod housing 80, locking lug 55 is simultaneouly being rotated out of engagement seat 100 of piston 35. Spring detent arm 50 and locking lug 55 are deflected downward as locking lug 55 rotates into contact with eccentrically radiused surface 107 of inner diameter 38. Lug 55 then snaps up into disengagement slot 110 by the recoiling action of spring arm detent 50 (FIG. 17).

Although rotational torque is applied in rotating actuating rod 45, axial rotation of piston 35 and incorporated seals 40 is prevented within inner diameter surface 32 by the normal friction existing between seals 40 in tight contact with inner diameter surface 32. Thus, piston 35 and seals 40 remain stationary within barrel tube 30 while locking lug 55 is rotated via rod 45, within inner diameter surface 38 of piston 35 during the disengagement of lug 55 from engagement seat 100 (FIGS. 4, 15, 16 and 17).

Lug return stop 115 permanently blocks locking lug 55 from being reversely rotated back into engagement seat 100 of piston 35. (FIGS. 4, 5 and 17). Thus, piston 35 and actuating rod 45 are permanently disconnected and cannot be reconnected. At this point in the sequence of operation, piston 35 is in touching contact with, but no longer mechanically connected to actuating rod 45. A forward pushing force upon rod 45 is translated to piston 35 and incorporated seals 40, thereby dispensing solution "S" (FIG. 5).

Figure 6:
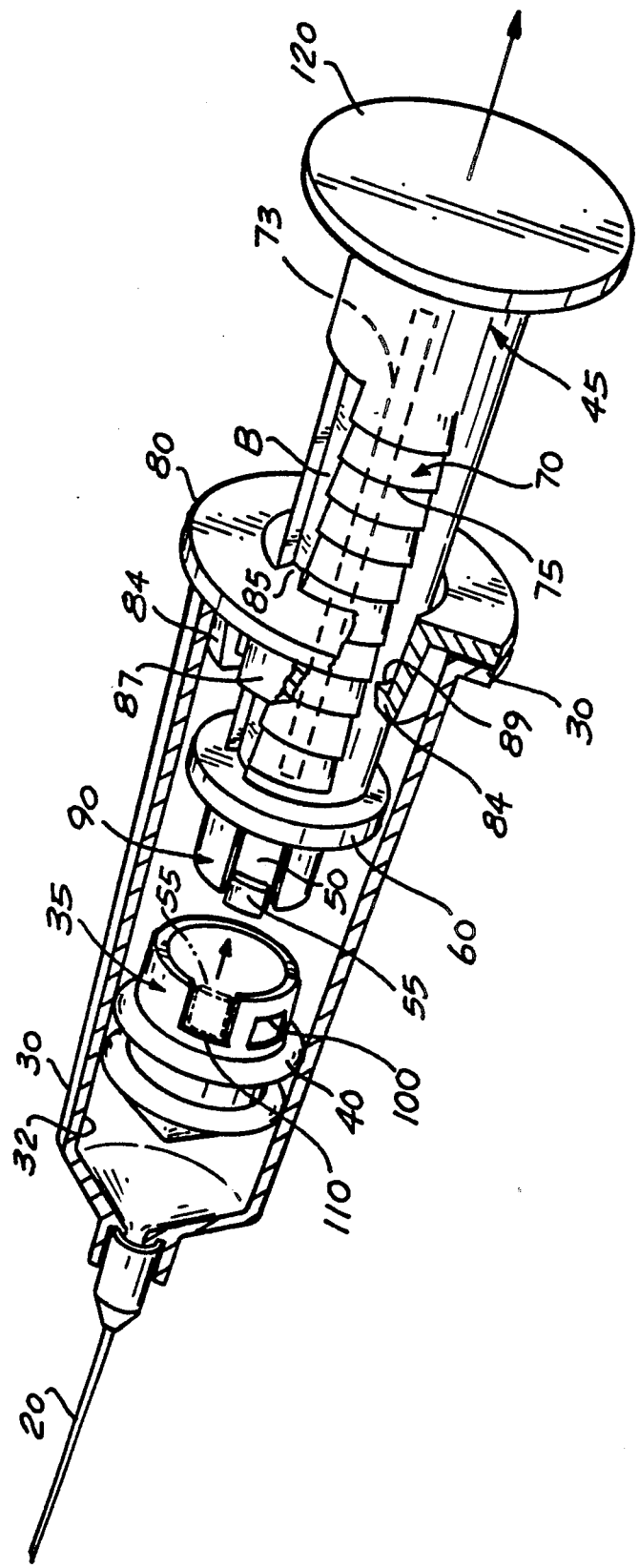
FIG. 6 is a sectional perspective view showing the actuating rod being separated from the piston as the rod is drawn to the rear in attempting a second aspiration or re-use of the syringe.

After dispensing solution "S", actuating rod 45 is shown being drawn to the rear in FIG. 6 in an attempt to re-use or re-aspirate the syringe 10. The disconnected piston 35 cannot follow actuating rod 45 in its rearward travel and remains stationary within barrel tube 30. Piston 35 cannot be reconnected to actuating rod 45 thereby making it impossible to re-aspirate or re-use the present invention for a second application. Therefore, the entire syringe 10, must be discarded after its initial and only use.

While the present invention as illustrated has been described with regards to the preferred embodiment, it is recognized that variations may be applied which do not depart from the spirit or intent of the present invention. For example, different methods of connecting and disconnecting the piston to and from the actuating rod can be used as well as variations of the methods of engagement and disengagement of the actuating rod teeth with the rod housing. Also, various methods of attaching the hollow needle to the barrel tube may be utilized, as well as attaching the needle to the barrel tube in some syringe applications while utilizing a detachable needle in others.

I claim:

1. A single use, self disabling syringe comprising an elongate barrel tube incorporating an internal smooth bore, a small opening at the distal end of said barrel tube constrictedly configured for a hollow needle to be affixed to said distal end; a plunger assembly axially disposed within said bore, said plunger assembly comprising a piston with incorporated seals of resilient material fitting snugly within said bore, an actuating rod connected to and extending from said piston and protruding through the proximal end of said barrel tube, said plunger assembly facilitates the initial aspiration and dispensing of a solution into and from said bore; a means for irreversibly disconnecting said piston from said actuating rod whereby aspiration of a solution into said bore is not possible once originally aspirated solution is partially or fully dispensed, said disconnecting means comprising a spring arm detent and a locking lug on said distal end of said actuating rod; and a lug engagement seat on said piston, radiused surface means for releasably interengaging said locking lug in said lug engagement seat, stop means for preventing reengagement of said lug in said seat, such that once disengaged, said lug cannot be reengaged in said seat.

2. The syringe of claim 1 further comprising a ratchet and pawl type detent for limiting forward movement of said plunger, wherein said detent includes a rod housing which functions in cooperation with said actuating rod, said rod housing being axially disposed within said proximal end of said bore such that said actuating rod moves reciprocatively within said rod housing.

3. The syringe of claim 1 wherein said syringe includes a safety shoulder cooperating between said actuating rod and said rod housing to block inadvertent or premature rotation of said actuating rod.

4. The syringe of claim 1 wherein said actuating rod is calibrated in combination with said rod housing such as to effect the aspiration and dispensing of whole or fractional volumetric quantities of a solution into and from said syringe.

5. The syringe of claim 2 wherein said detent, when in an engaged mode, prevents forward travel of said actuating rod and said piston within said bore.

6. The syringe of claim 2 wherein said detent, when in a disengaged mode, permits forward travel of said actuating rod and said piston within said bore.

7. The syringe of claim 1 wherein said actuating rod includes a plurality of guide tracks disposed along its axial length.

8. The syringe of claim 2 wherein said rod housing incorporates a guide pin, said guide pin, in cooperation with said guide tracks, effects straight line travel of said actuating rod in the rearward and forward directions within said bore.

9. The syringe of claim 2 wherein said actuating rod is disengaged from said rod housing when said actuating rod is rotated in a clockwise direction within said rod housing.

10. The syringe of claim 1 wherein said radiused surface means releasably disengages said locking lug from said seat once said actuating rod is rotated in the clockwise direction.

11. The syringe of claim 10 wherein said seals are in frictionally tight contact with said internal smooth bore of said barrel tube such that said seals prevent said piston from rotating about its longitudinal axis when said actuating rod is rotated within said piston.

12. The syringe of claim 10 wherein said disconnecting means has means creating an audible and a tactile click when said piston has been disconnected from said actuating rod by manual clockwise rotation of said actuating rod within said piston.

13. The syringe of claim 1 wherein said piston incorporates said stop means, said stop means comprising a return stop integral within said piston wall, said lug return stop preventing reconnection of said disconnected piston to said actuating rod.

14. The syringe of claim 2 wherein said actuating rod incorporates an integral travel stop, said travel stop limits rearward travel of said actuating rod within said barrel tube and prevents removal of said actuating rod from within said barrel tube.

15. The syringe of claim 1 wherein said plunger assembly is encapsulated within said barrel tube such that said piston is inaccessible once said syringe is fabricated at point of manufacture.

* * * * *